United States Patent
Kurzbuch et al.

(10) Patent No.: US 8,228,602 B2
(45) Date of Patent: Jul. 24, 2012

(54) SUPER CRITICAL ANGLE FLUORESCENCE SCANNING SYSTEM

(75) Inventors: Dirk Kurzbuch, Dublin (IE); Jim Writser Peter Bakker, Uppsala (SE); Thomas Ruckstuhl, Zurich (CH); Jonas Melin, Uppsala (SE)

(73) Assignee: Dublin City University of Collins Avenue, Dublin (IE)

( * ) Notice: Subject to any disclaimer, the term of this patent is extended or adjusted under 35 U.S.C. 154(b) by 320 days.

(21) Appl. No.: 12/732,053

(22) Filed: Mar. 25, 2010

(65) Prior Publication Data

US 2010/0243914 A1 Sep. 30, 2010

Related U.S. Application Data

(60) Provisional application No. 61/163,363, filed on Mar. 25, 2009.

(51) Int. Cl.
*G02B 21/26* (2006.01)

(52) U.S. Cl. .......................... 359/391; 359/393; 359/394

(58) Field of Classification Search ............... 250/458.1; 359/391; 435/7.92

See application file for complete search history.

(56) References Cited

U.S. PATENT DOCUMENTS

| | | | |
|---|---|---|---|
| 6,407,858 B1 * | 6/2002 | Montagu | 359/391 |
| 7,067,958 B2 | 6/2006 | Johansson et al. | |
| 2004/0209303 A1 * | 10/2004 | Martin | 435/6 |
| 2005/0285049 A1 * | 12/2005 | Montagu et al. | 250/458.1 |
| 2008/0160548 A1 * | 7/2008 | Klapproth | 435/7.92 |
| 2009/0211345 A1 * | 8/2009 | Nahm et al. | 73/61.55 |

OTHER PUBLICATIONS

Kurzbuch et al., "A Biochip Reader Using Super Critical Angle Fluorescence," Sensors and Actuators B 137:1-6, 2009.

* cited by examiner

*Primary Examiner* — Nikita Wells
*Assistant Examiner* — Johnnie L Smith
(74) *Attorney, Agent, or Firm* — Seed IP Law Group PLLC (57) ABSTRACT

A scanning system that provides for detection based on super-critical angle fluorescence (SAF) is described. The system provides for the optical coupling of a sample to the scanner in a sandwich structure that uses first and second refractive index matching materials to provide optical coupling through the sandwich arrangement.

19 Claims, 8 Drawing Sheets

SUPER CRITICAL ANGLE FLUORESCENCE SCANNING SYSTEM

CROSS REFERENCE TO RELATED APPLICATIONS

This application claims benefit under 35 U.S.C. 119(e) of U.S. Provisional Patent Application Ser. No. 61/163,363, filed Mar. 25, 2009 and entitled "SUPER CRITICAL ANGLE FLUORESCENCE SCANNING SYSTEM," which is incorporated herein by reference in its entirety.

FIELD OF THE INVENTION

The present invention relates to scanning systems and in particular to a scanning system that provides for detection based on supercritical angle fluorescence (SAF).

BACKGROUND

Point-of-care measurements require portable and inexpensive devices, that allow physicians to conduct diagnostic tests in the surgery and that have the potential for home self-testing. These devices need to be reliable and inexpensive, while still providing sufficient sensitivity for clinically relevant analytes. Currently, a significant number of markers are available for diagnosing and analyzing the progress of diseases using immunoassays. Furthermore, key biomarkers, for example for cardiovascular disease (CVD), are increasingly used for risk monitoring for individuals and populations, in order to predict the likelihood of developing specific diseases.

It is therefore desirable to be able to screen for a number of relevant analytes simultaneously on one platform for efficient risk stratification and disease diagnosis. Fluoro-immunoassays, using fluorescently labelled biomarkers, are a common method for screening and measuring analytes. These techniques typically involve patterned arrays of biorecognition elements which are imaged using an optical readout system. There is an increasing requirement to detect low levels of analyte in small volumes which necessitates the use of high sensitivity readout systems. Signal enhancement strategies for optical biochips include plasmonic enhancement, high brightness nanoparticles and the use of high collection efficiency optics.

Despite these known solutions there is still a need for a system and methodology that will provide for efficient detection of target analytes.

SUMMARY

These and other problems are addressed by a system and methodology in accordance with the present teaching that provides a scanning arrangement that is coupled to an optical element based on super critical angle fluorescence (SAF). By providing a scanning arrangement it is possible to provide fluorescence imaging of biochip arrays. The use of SAF not only provides substantial enhancement of the fluorescence collection efficiency but also confines the fluorescence detection volume strictly to the close proximity of the biochip surface, thereby discriminating against fluorescence background from the analyte solution.

By using SAF in combination with a scanning arrangement it is possible to provide increased detection sensitivity and decreased limit of detection (LOD) compared to conventional detection systems, by substantially increasing the light collection efficiency. Moreover, SAF detection allows the collection of the fluorescence only from molecules that are in close proximity to the interface of the substrate and the sample solution and not from the bulk solution. This important aspect of SAF leads to substantial reductions in background signal.

Desirably the scanning systems provides for multiplexed assay by combining a SAF-optical element and a scanning stage, typically a piezo-motor driven scanning stage. Such a system is particularly advantageous for point-of-care diagnostics and for use with disposable microfluidic substrates.

The scanning stage is desirably configured to provide for a scan in two dimensions which increases the area of the biochip which can be sampled. By suitably configuring the substrate on which the target analytes are operably optically coupled it is possible to provide a large number of reaction zones, resulting in a potential detection of more analytes on a single substrate than heretofore possible.

By suitably dimensioning individual reaction zones and providing for a scanning of the substrate using a laser it is possible to increase the density of the reaction zones on the surface of the substrate. By providing the substrate as a microfluidic chip, and as flow rates on a microfluidic chip may vary over a large area, it will be appreciated that this increase in density of the reaction zones provides for an equalisation of the sample flow rate across the surface area of the substrate.

Furthermore by using a laser scanning arrangement it is possible to reduce the dimensions of the individual reaction zones, meaning less reagent is required for analysis.

It will be appreciated that a combination of SAF and scanning allows scanning a surface while discriminating against bulk fluorescence from turbid samples/media.

Such a system may also be used to perform kinetic measurements. In this way continuous measurements at one or more locations on the sample substrate may be used to determine the rate of reaction. The increased luminescence detected over time is related to the reaction on the substrate. By monitoring the rate at which this luminescence changes it is possible to make determinations as to the this rate of reaction Accordingly, a first embodiment of the invention provides a scanning system comprising an optical detection system configured to provide an output signal based on emitted SAF from one or more target analytes provided as an array on a substrate, the substrate being moveable relative to the optical detection system so as to provide for a scanning of individual ones of the target analytes.

These and other features of the present teaching will be better understood with reference to the following Figures which are provided to assist the person skilled in the art in an understanding of the benefits and application of the present invention.

BRIEF DESCRIPTION OF THE DRAWINGS

The present invention will now be described with reference to the accompanying drawings in which.

DETAILED DESCRIPTION OF THE DRAWINGS

A scanning system provided in accordance with the present teaching provides for SAF excitation of target molecules. Such excitation allows for measuring in turbid media like whole blood, because excitation and detection takes place from below and only fluorescence in close proximity of the sample/chip interface is collected. It has known that that excited fluorescent molecules, which are in close proximity to the interface between two dielectric media, emit a large proportion of their radiation into the higher refractive index substrate. Moreover, the emitted light is highly anisotropic, with a substantial amount of fluorescence being emitted into angles above the critical angle as so-called SAF supercritical angle fluorescence.

Figure 1:
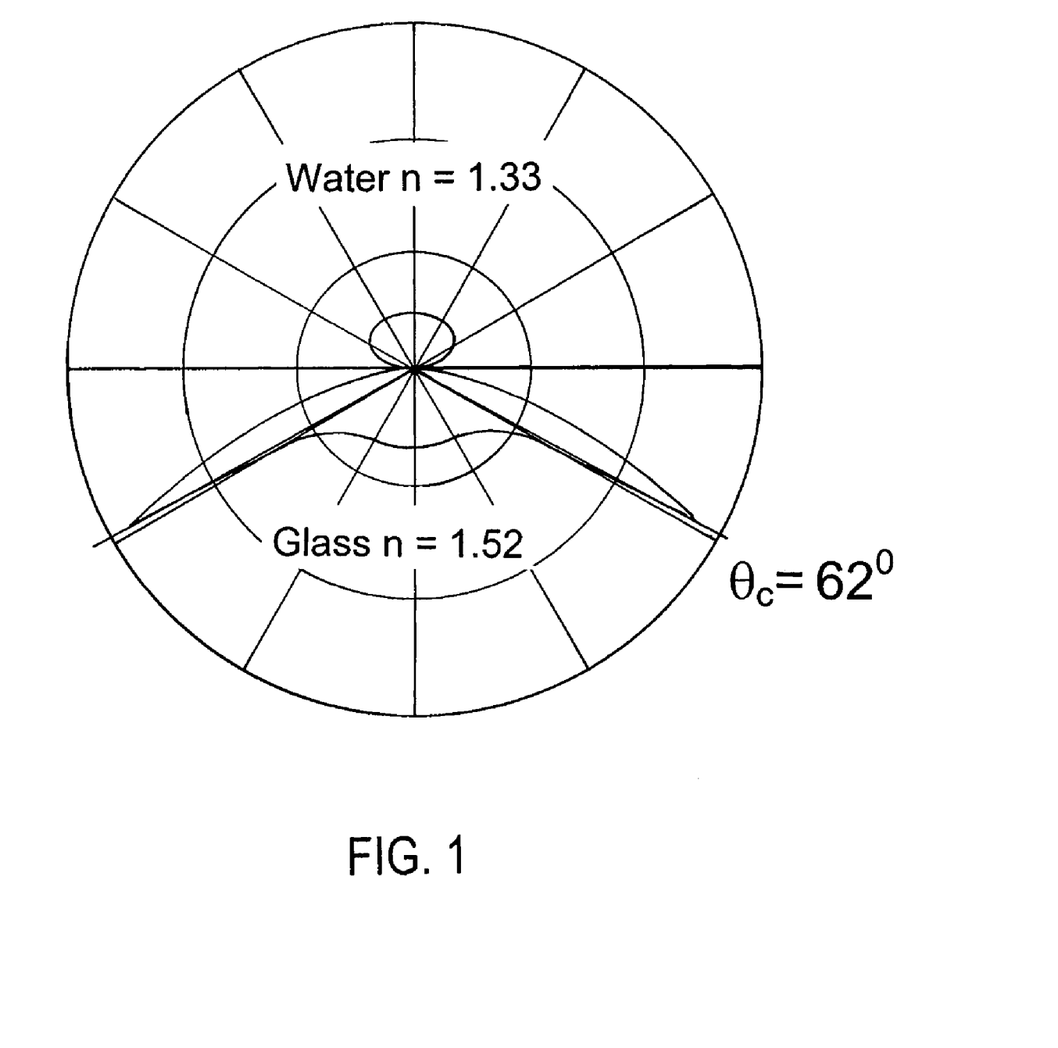
FIG. 1 shows an angular distribution of the fluorescence intensity of a molecule positioned at a water-glass interface averaged over all possible emission dipole orientations.

FIG. 1 shows an example of a modelled anisotropic light emission pattern for an air-glass system for the case of isotropic orientation of the molecular dipoles. It is evident that, a significant proportion or the light, (34% for isotropic orientation of dipoles) is emitted above the critical angle.

This effect can be modelled using classical electrodynamics. In brief, dipole emission (e.g. fluorescence) is composed of propagating waves that can be recorded in the far field but also of evanescent waves that decay rapidly within a short distance. The evanescent waves do not contribute to the radiant flux as long as the emitter is located in a medium of homogeneous index of refraction.

The situation changes substantially, however, when the emitter is positioned on top of a medium of larger index as is the case for fluorophores at the surface of a biochip. At sufficient proximity to the surface (of the order of the emission wavelength) the evanescent wave is converted into far field emission occurring inside the substrate above the critical angle, which constitutes the SAF emission. This fluorescence emanates only from molecules which are at short distance (~λ) from the surface, hence discriminating from bulk fluorescence in the sample solution. This feature allows selective detection of the analyte while significantly reducing background fluorescence.

Figure 2:
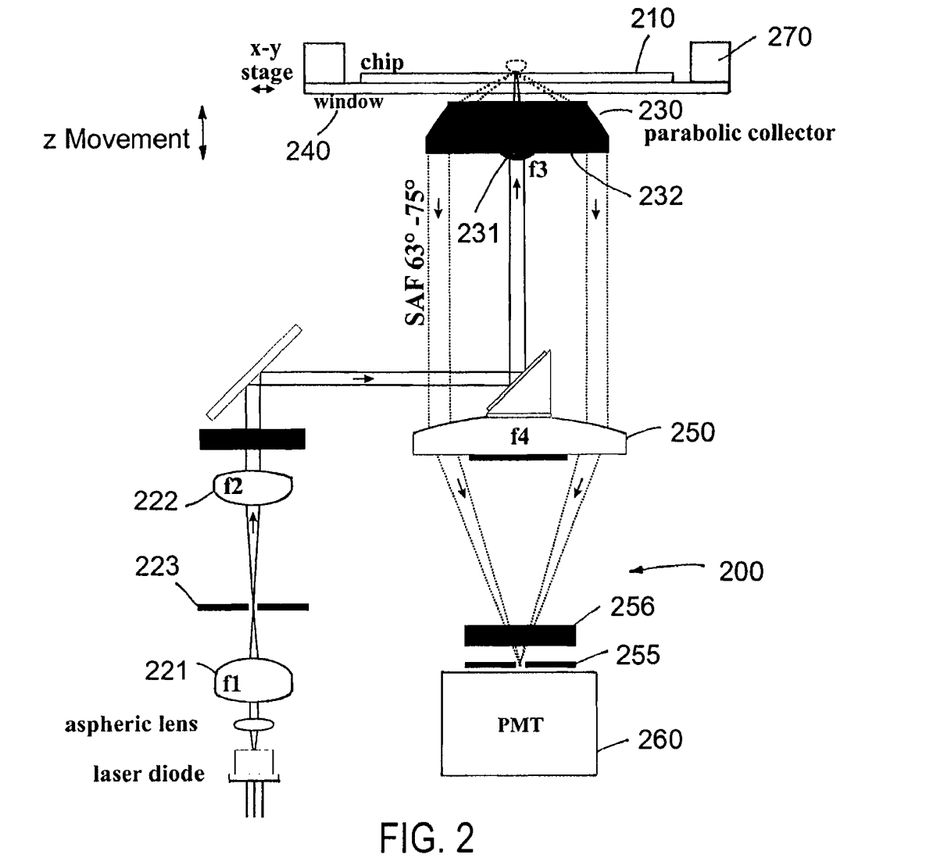
FIG. 2 is a schematic showing an SAF based scanner in accordance with the present teaching.

FIG. 2 shows an exemplary system 200 that may be used in accordance with the present teaching for concurrent sampling of multiple reaction zones. The system 200 is used to scan an array of fluorescent spots deposited on a Zeonor chip 210, made of an optical Cyclo Olefin co-polymer. The fluorescent spots used in this exemplary arrangement are either Cy5 or Alexa Fluor 647 molecules or biomolecules labeled with these dyes. A laser diode 220 (Roithner Lasertechnik, Austria) with a wavelength of 635 nm is used to excite the chip from below. Two achromatic lenses 221, 222 (focal lengths f1=20 mm and f2=40 mm) form a Keplerian beam expander to widen the beam. A pinhole 223 with a diameter of 100 μm is used to clean up the laser beam.

The SAF optical arrangement comprises a parabolic collector 230 made of Zeonex 480R, a high transmission, mouldable plastic, and features a diameter of 42 mm and a focal length of 6.25 mm. An aspheric surface 231 is incorporated into the element (f3=17 mm in material with nD=1.523), on a bottom surface 232 thereof, to focus excitation light onto the collection focus of the parabolic surface. In this way the excitation optical element components and the collection optical element component are integrally formed. This integration and the solid nature of the individual elements provides for accurate optical alignment between the excitation and collection optics and provides for a robust instrument.

Supercritical angle fluorescence emitted between 63° and 75° is collimated by total internal reflection at the parabolic surface which is surrounded by air. An upper surface 233 of the parabolic element 230 is optically coupled to a glass window 240 and in this exemplary arrangement, the glass window and the Zeonor chip is optically coupled using immersion oil (nD=1.517, Cargille Labs, USA).

A plano-convex lens 250 (f4=150 mm, diameter=50 mm) is used to focus the emitted fluorescence through a detection aperture 255 onto the photocathode of a photomultiplier 260 (H8259-02 PMT module, Hamamatsu, Japan), which is run in a preset counting mode. A combination of an interference filter 256 (FF01-676/29-25, Semrock Inc., USA) and detection aperture 255 (diameter=800 μm) is used to block excitation light.

Figure 3:
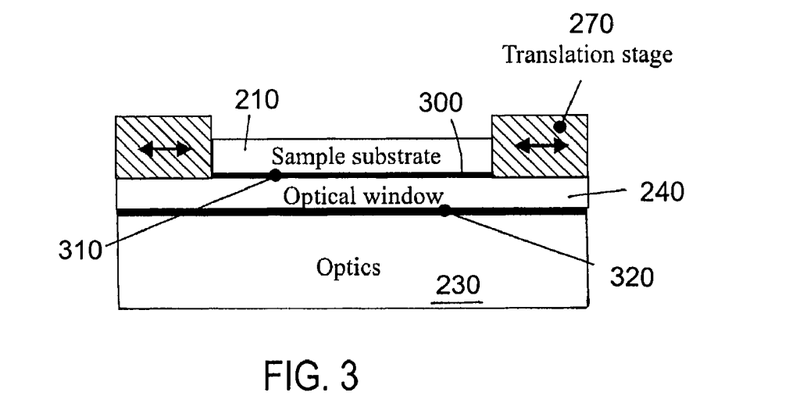
FIG. 3 is a detailed view of the mounting of the biochip relative to the optical detection arrangement.

FIG. 3 shows a detailed view of the relative positioning of the mounting of the biochip to the optical detection system components. A sandwich structure is provided having three distinct components. The sample substrate 210 which may be provided in any one of a number of different configurations (for example a planar substrate or a microfluidic chip) is optically coupled via a first index matching material 310 to a glass window 240 which is then optically coupled via a second index matching material 320 to the collection optics, particularly the parabolic collector 230 (shown in FIG. 2). Once mounted, the substrate 210 is maintained in position relative to the glass window 240 using a spring or other biasing mechanism to maintain the optical contact. The glass window 240 is however moveable relative to the parabolic collector so as to achieve a scanning of the sample provided on the substrate 210. As the substrate is fixed relative to the glass window, any movement of the window will effect a corresponding movement of the substrate—although desirably there is no relative movement between the window and the substrate.

Scanning the sample is achieved by moving the combined substrate (or biochip) and glass window (0.99 mm) arrangement. The coupled arrangement is desirably mounted on a metallic holder over the top of the parabola collector by a piezo-motor-driven XY-stage. In this arrangement, the bottom 300 of the sample substrate is in optical contact with the window by using an index-matched transparent immersion oil 310, the first index matching material. A second index matching material 320 is provided between the window 240 and optics 230 to establish an optical connection and allow the window to be moved in the horizontal plane. The optics focuses light from a light source through window and substrate onto the sample surface and guides light from the sample to the detector. Illumination of and/or light collection from the sample is performed at large surface angles. A translation stage 270 moves substrate and window horizontally over the optics which are maintained in a fixed position. By this means arbitrary surface regions of the sample can be measured. The translation stage desirable allows for movement in both the X and Y planes. The gap between parabola and glass window is permanently filled with refractive index matching oil which allows scanning large areas (centimeters) at high speed on the biochip without the requirement of a dynamic autofocus control and without losing optical contact. Furthermore the holder of the parabolic element is desirably configured to allow vertical movement of the parabolic element relative to the biochip. This allows (due to the optical contact maintained through the use of the index matching oil) for an adjustment of the parabolic element and laser focus to a slight extent (about ±100 micrometer).

Figure 4:
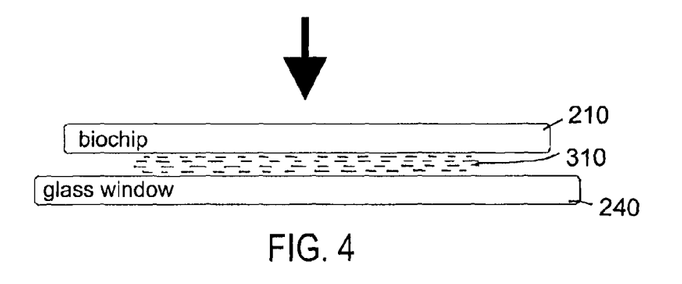
FIG. 4 shows a biochip being brought into optical contact with a glass window.

It will be appreciated that by using an immersion oil between the parts that are moveable relative to one another that such movement is possible. In such an arrangement the biochip is optically coupled to the window using a first index matching material 310—as shown in FIG. 4—while the window is coupled to the optics using a second index matching material. The first and second index matching materials may be the same, typically immersion oil 320. The viscous nature of the immersion oil does not restrict relative movement between each of the moveable elements of the system.

Translational Movement

The XY translation movement of the biochip relative to the optical components is desirably provided by mounting the biochip on a moveable stage. This stage may be desirably driven by a piezoelectric arrangement. In an exemplary arrangement the stage utilizes piezomotors based on the Piezo-LEGS technology developed by PiezoMotor AB (such as that described in S. Johansson, M. Bexell, and A. Jansson, *Wide Frequency Range Electromechanical Actuator*, P. U. A. (SE), Editor. 2005.), which is based on 'legs' of piezoceramic material, which move a drive rod by a walking motion. Using this technology, motion can be controlled down to the nanometer range, while enabling movement over distances of several mm or more. The main advantage of using such a piezomotor is that these motors are small and can be produced at a relatively low price, which makes them suitable for use in a point-of-care instrument. The stage is designed to make the chip accessible from both sides, thus facilitating assay measurements with the chip already in the reader. In this way the excitation of a sample and collection of the resultant luminescence is achieved from the same side of the sample, such that a user can add sample material to the substrate while the substrate is in position within the scanner. As was mentioned above, the biochip may also be moved in a vertical or Z direction relative to the optical module.

Positioning of the chip is controlled by position encoders based on magnetic scales and a controller unit produced by Nanos Instruments (Germany). The controller is interfaced to a PC through a counter/timer card (PCI-6602, National Instruments, USA). The pulses produced by the position encoder are also used as triggers for writing the photon count from the PMT to the buffer, effectively position-tagging the measured values with a resolution down to the order of 10s of nanometers.

Biochip

Figure 5A:
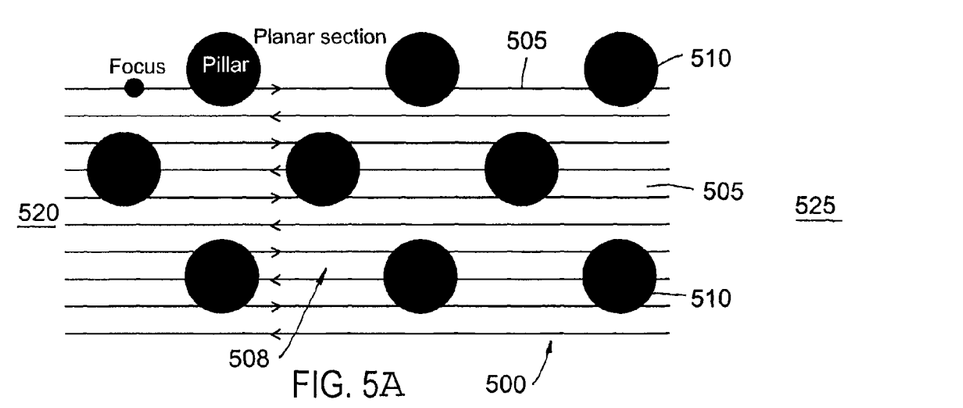
FIG. 5A is a plan view of an upper surface of a biochip.
Figure 5B:
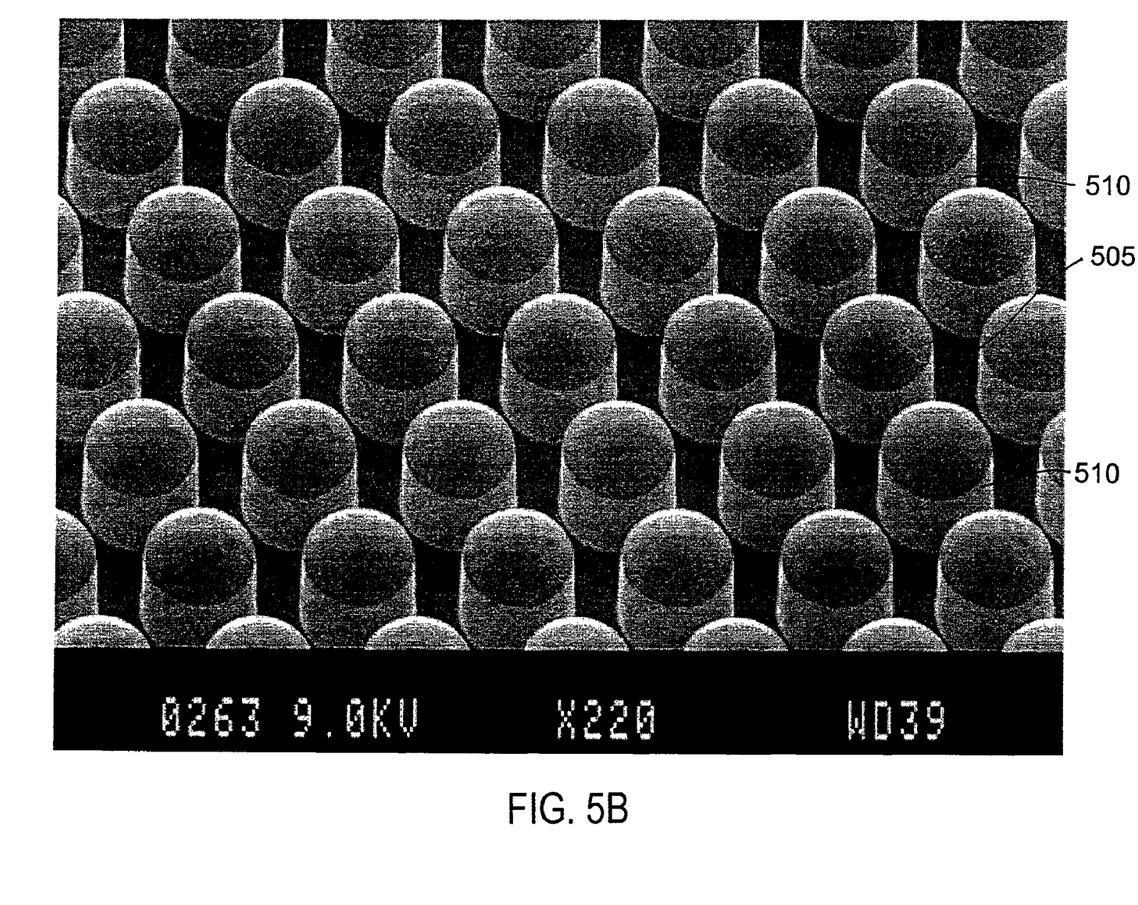
FIG. 5B is an image showing a perspective view of a portion of a biochip shown in FIG. 5A.

While any substrate material or configuration could be used for locating a sample for subsequent analysis in a preferred arrangement the substrate was provided in the form of an open lateral flow planar chip. Such polymer biochips were injection moulded by Åmic AB (Uppsala, Sweden) using an optical Cyclo Olefin coPolymer (Zeonor 1060R, Zeon, Japan) resulting in disposable planar chips with a microscope slide format (75×25×1.2 mm). These chips were used in order to evaluate the optical setup as well as the scanning system. The chips were oxidized in oxygen plasma for 6 min at a working pressure of 0.26 mbar, 1000 W and with a flow of oxygen at 100 ml/min. The chips were then immersed in a solution of 3 vol % APTES in 95% ethanol for 2 hours. Curing took place in air at room temperature which allowed for cross-linking of the silane resulting in a stable amino-functionalized surface which was reactive towards, for example, ester functionalised fluorophores. APTES-coated surfaces were sequentially immersed in an oxidized 2% dextran solution for 2 hours and further oxidized in 30 mM $NaIO_4$ for 2 hours. The resultant aldehyde surface enables immobilization of amino functionalized molecules such as proteins As shown in FIG. 5 an exemplary biochip 500 provided as a microfluidic structure comprises a substantially planar substrate 505 having a plurality of reaction zones 508. Projecting upwardly from an upper surface 515 of the substrate are a plurality of pillars 510. The pillars 510 serve to break up the upper surface of the substrate to define a plurality of fluid paths, and as a result of the relative geometries of the microfluidic structure generate capillary forces that allow for a fluid introduced at a first end 520 of the substrate to progress through to a second end 525. As shown in FIG. 5B the individual pillars are upstanding from an upper surface 515 of the substrate. In use, flurophores are bound to the surface of the reaction zones and luminescence resultant from excitation of these flurophores will be optically coupled through the substrate to a detector below a lower surface 520 of the substrate. The flurophores are generated by initially providing one or more bio-recognition elements on the surface of the substrate that will preferentially couple to analyte within a fluid sample flowing passed the reaction zones. In the context of a SAF collection system, the luminescence originating from the planar surface of the substrate will be preferentially collected.

Figure 6:
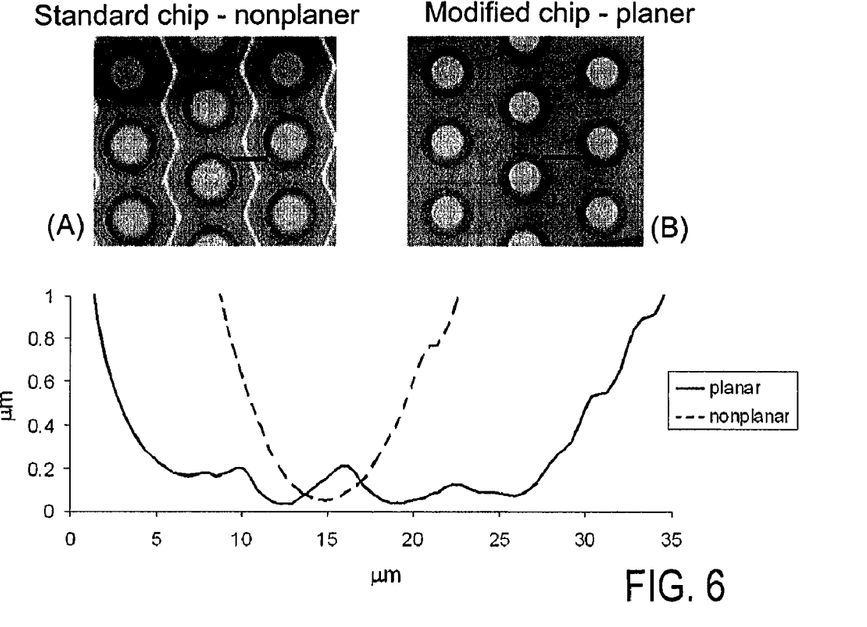
FIG. 6 is shows two exemplary arrangements for sidewalls of a individual pillars provided on an upper surface of a biochip.

The geometry of the individual pillars may be configured to have sloped side walls. In such an arrangement the side walls will desirably slope inwardly from the base of each pillar to the top of the individual pillars. Desirably and as shown in FIG. 6B, the side walls are substantially vertical and are parallel with one another. In this way the spacing between individual pillars may be increased—as is shown in FIG. 6C. By providing such a geometry it is possible to increase the density of the reaction zones on the surface of the substrate and yet maintain a fluid path between the individual pillars. When the substrate is provided as a microfluidic chip, it will be appreciated that this increase in density of the reaction zones provides for more fluid paths per unit area. Within a microfluidic device the greater the surface area of the device the greater the discrepancy in the sample flow rate across through individual fluid paths. By increasing the number of fluid paths per unit area, it is possible to ensure that the sample flow rate through each of the individual fluid paths is substantially equal.

In order to demonstrate the imaging capabilities and surface selectivity of the system, a pattern of surface-bound fluorophores was created and measured with different concentrations in the bulk superstrate. A solution of 1 µg/ml Alexa Fluor 647 succinimidyl ester was spotted on Zeonor slides which had been functionalized with APTES, to form the letters BDI (abbreviation for Biomedical Diagnostics Institute). The pattern covers an area of approximately 4.5×2.5 mm. After spotting, the slides were sonicated in a 0.1% SDS solution for 10 minutes to remove any unbound fluorophore. In order to demonstrate the ability of the SAF system to discriminate against bulk fluorescence from the superstrate, a pattern was measured in the SAF scanner with a superstrate solution of Alexa Fluor 647 in concentrations varying from 1 ng/ml to 1 µg/ml. The scanning was performed by moving the sample in a meander pattern such as left and right a shown by the arrows of FIG. 5A.

Kinetic Measurement

To explore the possibility of performing kinetic measurements on this optical setup, time resolved experiments were made. Streptavidin was deposited on dextran-functionalized COP slides in a line perpendicular to the scanning direction. The spotting solution contained 1 vol % trehalose (Sigma Aldrich), 50 mM $NaPO_4$ buffer (pH 7.5, Sigma Aldrich) and 0.5 mg/ml streptavidin (Sigma Aldrich). The mixture was spotted under humid conditions (relative humidity 70%) with a sciFLEXARRAYER S3 (Scienion, Germany), resulting in a ~0.4×4.0 mm band. The dextran surface surrounding the streptavidin line was blocked with bovine serum albumin (BSA) (Sigma Aldrich, 5 mg/ml, 20 min) and washed in Milli-Q water, to rinse off any non immobilized streptavidin.

Biotin Cadaverine (Sigma Aldrich) was conjugated to Cy5 NHS ester (Amersham Biosciences) in DMSO by adding triethylamine for one hour. The conjugate was purified on a Sephadex LH20 column (Amersham Biosciences) by collecting the first ~500 µl of the coloured fraction. The concentration of the conjugate was determined by preparing a standard curve of Cy5 NHS Ester dye by diluting it in steps of five (resulting in 205, 41.1, 8.21, 1.64, 0.329 and 0 nM). An aliquot of the conjugate was diluted by a factor of 100. Based on the standard curve, we evaluated the concentration to be 11 mM. For biotin assay experiments the biotin conjugate was diluted to 2.2, 1.1, 0.22, 0.044 nM. In an assay experiment, the scanner was operated in line-scanning mode (~2 sec/line) across the streptavidin line, resulting in data collection also from areas with no biotin. After a few seconds of scanning, 40 µl of biotin solution was dispensed on the chip and data was recorded for about 3.5 minutes. A new chip was used for each experiment.

Imaging Resolution and Limit of Detection (LOD)

Figure 7:
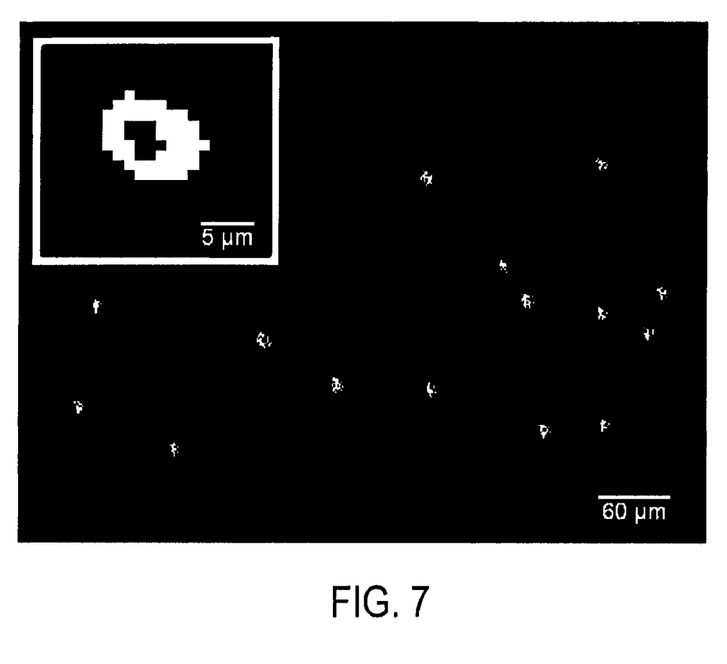
FIG. 7 is a confocal image of 200 nm beads at an excitation wavelength of 625 nm to illustrate the resolution of the instrument with the inset on the top left shows the experimental point spread function

To investigate the imaging performance of the instrument, fluorescent beads (200 nm, dark red 660/680-F8807, Invitrogen) were used as point emitters to enable determination of the instrumental point spread function. The beads were diluted in PBS to a concentration of 500 ng/ml and a droplet of 40 µl was dispensed with a pipette on an unfunctionalized Zeonor slide and this area was scanned repeatedly. FIG. 7 shows the scanned image. Each line was scanned with a step length of 1 µm. The point spread function was determined by forming a superposition of 10 images of single beads. The diameter averages at about 5 µm, which represents the resolution of the instrument.

Figure 8:
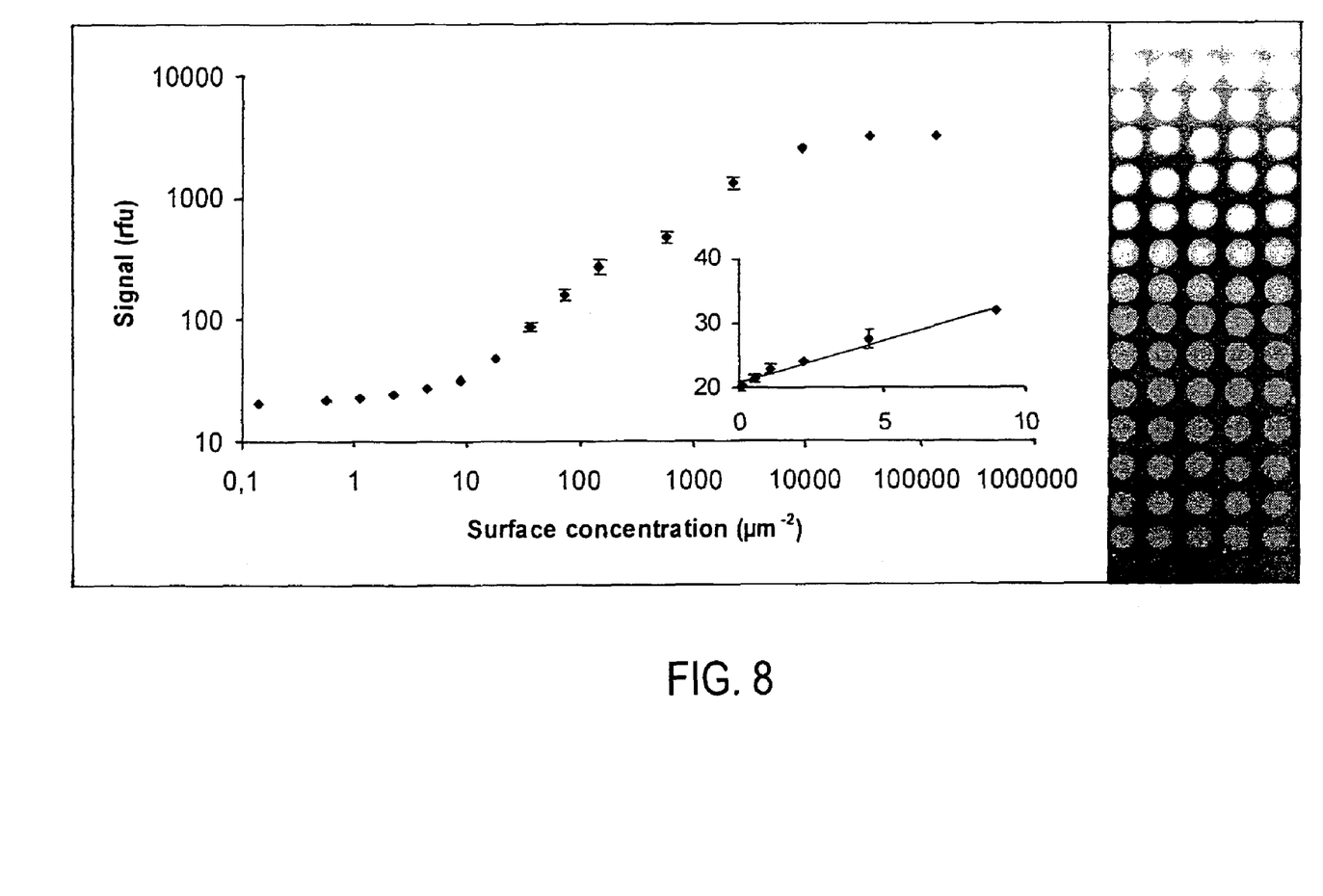
FIG. 8 shows a scan image from the SAF scanner of a planar substrate with spots of different fluorophore concentrations with the accompanying graph showing the relative intensities plotted, a further additional graph provides a double logarithmic plot of the signal against the fluorophore surface concentration on the substrate, the insert shows the six lowest concentrations in a linear plot with standard deviations calculated from six replicates.

To determine a generic limit of detection for the instrument, a microarray of fluorescent spots (Cy5) on a calibration slide with different concentrations of dye molecules per square micrometer (Full Moon BioSystems, USA) was scanned. The results are shown in FIGS. 8(*a*) and 8(*b*) with FIG. 8*b* showing a scanned image of the calibration slide with the logarithm of the intensities. This is the slide with the spotted concentrations of fluorpophore. The concentrations range from 0.0, 0.14, 0.56, 1.12 up to 36750 $\mu m^2$ in the columns from left to the right in FIG. 8*a*. An area of 5.1 mm×2.0 mm was scanned and the spot intensities were determined by using an edge detection method and integration of the spots. The limit of detection was determined to be approximately 0.14 fluorophores per $\mu m^2$, which is a clear indication of the high sensitivity of the system.

Since the SAF emission profile depends strongly on the medium on top of the glass/sample interface and because the optics of this exemplary arrangement are optimized for aqueous solutions ($n_D$=1.33), an improved signal-background ratio should in principle be achievable under aqueous conditions. This was investigated experimentally by scanning spots of covalently bound Alexa Fluor 647-dyes on APTES-coated chips which were either covered with water or exposed to air only. An average 1.31-fold increase in signal for water compared to air was obtained with a 1.10-fold increase in noise level which corresponds to the predictions of the theory of SAF.

Surface Selectivity

Figure 9:
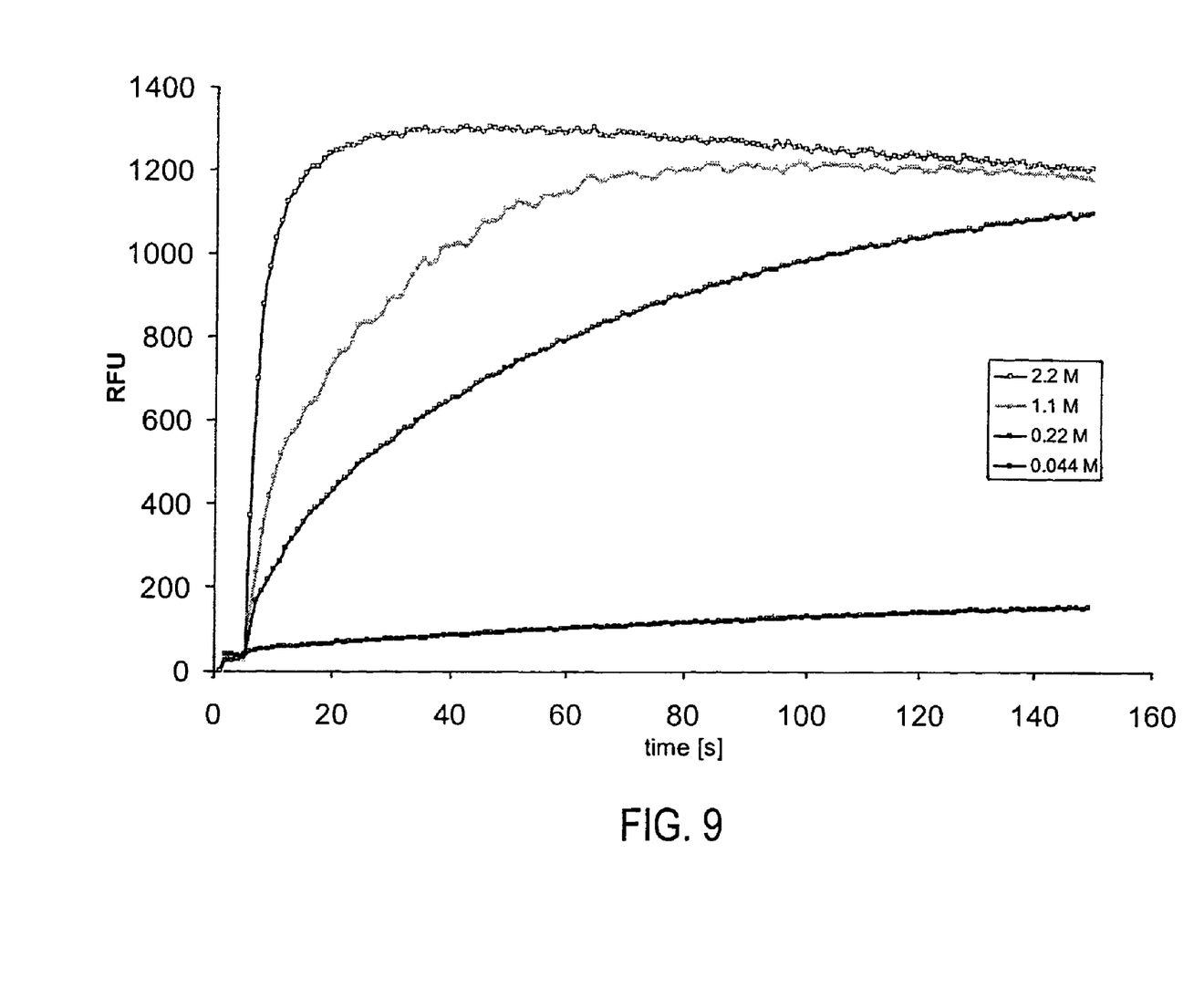
FIG. 9 shows binding curves for four different analyte concentration (2.2, 1.1, 0.22, 0.044 nM) and control resulting from a use of the scanner in kinetic measurements.
Figure 10:
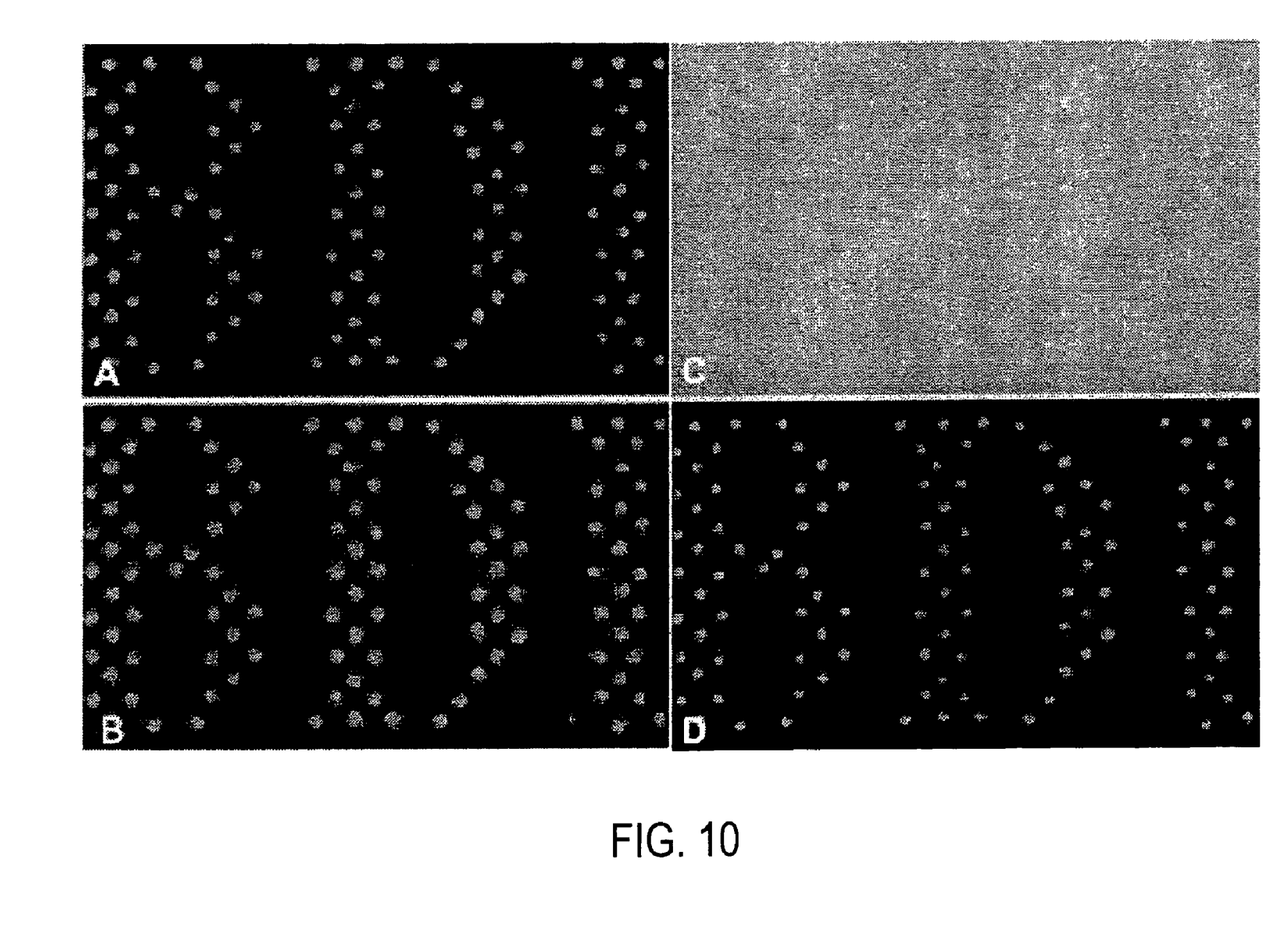
FIG. 10 shows surface confined imaging using the example in Images A, B and C of the BDI pattern with increasing concentration of fluorophores in the superstrate (10, 100 and 1000 ng/ml respectively and Image D showing the result after the high concentration fluorophore solution was removed and replaced by water.

The combination of SAF detection and scanning of the focus position allows for surface selective imaging of fluorophores in the near field. To demonstrate this, a pattern of surface immobilized fluorophores with different concentrations of free fluorophores in the bulk superstrate were imaged. The results are shown in FIG. 9. In order to more clearly visualize the 10-fold increase in the bulk concentration, the images show the logarithm of the recorded intensity. The first three images (FIGS. 9*a*-9*c*) show the measurements with increasing concentration of fluorophore in the superstrate, i.e. 10, 100 and 1000 ng/ml. These bulk concentrations correspond to 1.18, 11.8 and 118 fluorophores/$\mu m^2$ in the near field (i.e. within a distance from the surface of one third of the emission wavelength). The pattern remains clearly visible as the fluorophore concentration in the bulk increases, until the number of bulk fluorophores in the near field becomes comparable to the surface concentration of immobilized fluorophores (FIG. 9C). FIG. 9D shows the result after the high concentration fluorophore solution was removed and replaced by water. The reversion back to a clearly visible pattern indicates that free bulk fluorophores, not surface bound species, are responsible for the increase in background. Some faint fluorescence signals can however be observed in between the pattern, as a result of non specific adsorption of fluorophores. Most of the background is probably a result of Rayleigh scattered photons passing the emission filter, scattered excitation light of the laser beam and the thermoelectric noise of the PMT The surface-confined SAF detection principle enables real time measurements of biomolecular binding reactions on the imaged surface. We demonstrate this capability using a model system of surface-immobilized streptavidin in combination with fluorescently labelled biotin. The results are shown in FIG. 10. The scanning readout format means that the areas with and without immobilized streptavidin can be monitored in the same experiment. The signal originating from nonspecific adsorption of biotin or biotin free in solution can therefore be compensated for by subtracting the intensity recoded for areas without immobilized streptavidin. If a high concentration of biotin (2.2 nM) is used, the addition of labelled analyte to the surface is visible as a rapid increase in signal intensity to a maximum level, reflecting a quick saturation of all available binding sites of the streptavidin. After reaching the maximum level, a small decrease in signal intensity can be observed over time. This is most likely the result of dissociation of non immobilized streptavidin from the surface or bleaching of the captured fluorophores. For lower concentrations, the signal increase after biotin addition is less rapid, as a result of slower reaction kinetics and diffusion rates at lower concentrations.

We have described here a low-cost, supercritical angle fluorescence chip reader for rapid biochip analysis, which is suitable for point of care testing. The developed system exhibits a number of significant analytical performance features based primarily on exploitation of the SAF principle. In particular, the combination of the high collection efficiency and the surface selectivity of the SAF detection technique yields a generic LOD of 0.14 Cy5 fluorophores per $\mu m^2$. This represents a very low instrumental limit which is expected to lead to very low LOD's in real assays when appropriate measures for reducing non-specific binding are implemented. A scan range of 5 mm×7 mm was achieved with high speed and high precision, using a low cost, miniature xy stage. We have also demonstrated the use of the scanner for real time binding reactions.

The optical coupling using both first and second index matching materials allows for a static mounting of a sample substrate onto an optical window that may then be moved relative to collection optics to allow for a scanning of the substrate In the arrangement described herein, excitation of the sample and detection of the resultant luminescence is effected from below the sample substrate and the sample substrate is moveable relative to the optical detection system. By providing a support window between each of the substrate and the optical detection system it is possible to provide such an arrangement. The substrate is optically coupled to the support window via a first optical interface and once coupled relative movement of the substrate and the support window is not expected. The support window however is configured to be moveable relative to the collection optics so as to allow for scanning of the substrate and to allow for such lateral movement while maintaining optical contact, a refractive index matched fluid is provided between each of the support window and the collection optics. Such a sandwich structure allows for accurate optical alignment of the components to allow for rapid and accurate scanning of a sample. By maintaining one side of the sandwich in a fixed relationship and having the other side moveable, it is possible to accurately and quickly scan across a substrate without having to contact the substrate.

It will be appreciated that the sample substrate described herein with reference to the SAF scanner arrangement has been described in the context of a microfluidic device. Such a device is advantageous in that the volume of sample required for particular analysis is reduced and as a result such devices are particularly suited for point of care applications. In the context of blood sampling it is possible using the teaching of the present invention to draw the blood from a patient and then analyse that blood sample contemporaneously. The use of an open lateral flow chip—such as that described herein— is useful within the context of the present teaching but it will be understood that other microfluidic devices such as those comprising an optically transparent surface through which generated luminescence may propagate could also be used.

A scanning system such as that described herein could also be usefully employed with non-microfluidic substrates. It will be understood that exemplary arrangements of a scanning system that provides for detection based on supercritical angle fluorescence (SAF) has been described. The system provides for the optical coupling of a sample to the scanner in a sandwich structure that uses first and second refractive index matching materials to provide optical coupling through the sandwich arrangement. Where one or more features have been described with reference to one or more Figures it will be appreciated and understood that modifications could be made to that described herein without departing from the spirit and or scope of the invention which is to be limited only as is deemed necessary in the light of the appended claims.

Furthermore, the words comprises/comprising when used in this specification are to specify the presence of stated features, integers, steps or components but does not preclude the presence or addition of one or more other features, integers, steps, components or groups thereof.

The invention claimed is:

1. A luminescence based optical scanning system for detecting light emitted from a sample provided on a substrate, the system comprising:
   a. An optical excitation module for providing an excitation signal to two or more sample sites provided on the substrate;
   b. An optical detection module configured to detect supercritical angle fluorescence emitted by an excited sample;
   c. A mount for receiving the substrate, the mount comprising a support window provided between the optical detection module and the received substrate, the support window being optically coupled to at least one element of the optical detection module via a first index matching material and being optically coupled to the received substrate via a second index matching material, the mount providing for lateral movement of the substrate relative to the each of the optical excitation and optical detection modules so as to allow for sampling at each of the two or more sample sites.

2. The system of claim 1 wherein the substrate comprises a plurality of flow paths, the two or more samples sites being provided at distinct locations within the flow paths.

3. The system of claim 2 wherein substrate is a lateral flow device.

4. The system of claim 1 wherein the optical detection module and optical excitation module comprise a parabolic collector provided relative to the substrate such that luminescent light entering the parabolic collector at angles greater than the critical angle is collimated by total internal reflection at internal surfaces of the parabolic collector.

5. The system of claim 4 comprising an integrated aspheric optical element provided on a lower planar surface of the parabolic collector, the aspheric optical element being configured to focus excitation light onto the collection focus of the parabolic collector.

6. The system of claim 4 wherein the substrate is arranged relative to the parabolic collector such that the two or more samples are provided at the collection focus of the parabolic collector.

7. The system of claim 4 wherein the optical detection module comprises an optical element provided to focus light exiting from the parabolic collector onto a detector.

8. The system of claim 7 wherein the detector is a photomultiplier.

9. The system of claim 5 wherein the optical excitation module comprise a lasing device configured to provide an optical excitation signal, the aspheric element being provided in the optical path between the lasing device and the substrate.

10. The system of claim 1 wherein the support window is moveable in both x and y directions relative to each of the optical excitation and optical detection modules.

11. The system of claim 1 wherein the support window is moveable in a vertical direction relative to each of the optical excitation and optical detection modules.

12. The system of claim 1 wherein the substrate is an open lateral flow microfluidic device comprising a plurality of pillars upstanding from an upper surface of the device, the pillars defining the flow paths therebetween.

13. The system of claim 12 wherein side walls of the pillars are substantially parallel with one another.

14. The system of claim 1 wherein the mount comprises a piezomotor.

15. The system of claim 1 comprising biasing means for biasing the substrate into optical contact with the support window.

16. A luminescence based optical scanning system for detecting light emitted from two or more samples provided at distinct locations on a single substrate, the system comprising:
   a. An optical excitation module for providing an excitation signal to the two or more samples;
   b. An optical detection module configured to detect super-critical angle fluorescence emitted by an excited sample; and
   c. A mount for receiving the substrate, the mount providing for lateral movement of the substrate relative to the each of the optical excitation and optical detection modules so as allow for sampling of each of the two or more samples.

17. The system of claim 16 wherein the substrate comprises a microfluidic device having a plurality of flow paths, the two or more samples being provided at distinct locations within the flow paths.

18. An optical interface for use in coupling a sample substrate to a SAF scanning system, the interface providing an optical coupling between the substrate and a detection module of the scanning system; the interface being moveable relative to the detection system in at least two directions to allow for scanning of discrete regions of the sample substrate and wherein the sample substrate is optically coupled to the interface using a first index matching material and the optical interface is optically coupled to the detection system via a second index matching material.

19. A super critical angle fluorescence based optical scanning system for detecting florescence emitted from two or more samples provided at distinct locations on a single substrate, the system comprising:
   a. An optical excitation module for providing an excitation signal to the two or more samples;
   b. An optical detection module configured to detect super-critical angle fluorescence emitted by an excited sample;
   c. A mount for receiving the substrate, the mount providing for lateral movement of the substrate relative to the each of the optical excitation and optical detection modules so as allow for sampling of each of the two or more samples, and
   wherein the optical excitation module and optical detection module comprises a parabolic collector integrated with an aspheric optical element.

* * * * *